United States Patent [19]

Geistlich et al.

[11] 4,096,241
[45] Jun. 20, 1978

[54] TOOTH PREPARATIONS

[75] Inventors: Peter Geistlich, Stansstadt; Rolf Pfirrmann, Lucerne, both of Switzerland

[73] Assignee: Ed. Geistlich Sohne A.G. fur Chemische Industrie, Lucerne, Switzerland

[21] Appl. No.: 699,328

[22] Filed: Jun. 24, 1976

[30] Foreign Application Priority Data

Jun. 24, 1975   United Kingdom ............... 26767/75

[51] Int. Cl.$^2$ .............................................. A61K 7/22
[52] U.S. Cl. ...................................................... 424/54
[58] Field of Search ...................................... 424/49–58, 424/334

[56] References Cited

U.S. PATENT DOCUMENTS

| 1,211,712 | 1/1917 | Keefe | 424/49 |
|---|---|---|---|
| 1,275,779 | 8/1918 | Spies et al. | 424/49 |
| 1,318,254 | 10/1919 | Andresen | 424/334 |
| 1,417,091 | 5/1922 | Miller | 424/334 |
| 1,551,638 | 9/1925 | Brady | 424/334 |
| 2,004,957 | 6/1935 | Messner | 424/38 |
| 2,347,567 | 4/1944 | Kresse | 424/334 |
| 2,527,686 | 10/1950 | Sandberg | 424/334 |
| 3,886,269 | 5/1975 | Trujillo | 424/334 |

FOREIGN PATENT DOCUMENTS 1,124,285   8/1968   United Kingdom.

OTHER PUBLICATIONS

Reeves; D. S. Schwettzer, F.A.W. Experimental Studies with an Antibacterial Substance, Taurolin, Proc. 8th Int. Congress of Chemotherapy, Athons, 1973, II:5-83–586 (1947) Daikas, George k(ed) per Chem. Abstr., 84:39312N.

Strub, J. R., Doct. Diss. Zurich (1975) Plaquebildungshemmung Durch Spulen mit 3 Antibakteriellen Mitteln. Geistlich Sohne, Wolhusen. Data Sheets on Taurolin.

Muhlemann; H. R., Strub; J. R., Helv. Odont. Acta 19(2):57–60, Oct. 1975, "Inhibition of Plaque Growth with Taurolin, Vantocil and Amine Fluoride".

Ayrton de Toledo, Orlando et al., Revista Fac. Farm. Odont. Araraquara 3(2):267–288 (1969) Effect of Formaldehyde Containing Drugs on the Dental Pulp of Rat Molars.

Primary Examiner—Shep K. Rose
Attorney, Agent, or Firm—Bacon & Thomas

[57] ABSTRACT

This invention relates to novel preparations for the treatment and for prophylaxis of tooth and gum infections, and in particular parodontosis, comprising derivatives of thiadiazine as active ingredient. Pharmaceutical compositions according to the invention are described and exemplified.

6 Claims, No Drawings

TOOTH PREPARATIONS

This invention relates to novel preparations for the treatment of tooth and gum infections and in particular parodontosis.

Parodontosis is a progressive, chronic inflammatory infection of the immediate surroundings of the tooth root and the tooth bed (parodontium). This disease, which is increasingly common in men and women over 30 years of age, successively establishes itself in the gingival border, the periodontal membrane and the osseous tooth socket.

A healthy gum lies firmly around the neck of the tooth, but when circulation disorders occur, it becomes flaccid, tends to bleed and loosens itself from the tooth, producing a gingival pocket.

Parodontosis is caused by a bacteria and their metabolic products and it is associated with the build up of tartar and bacterial plaque. We have now found that, although tooth preparations have commonly contained bactericides for many years, without affording significant protection against parodontosis, one particular class of bactericides is very effective. We believe that this effectiveness is due to the unique action of the compounds concerned not only against the bacteria but also against the toxins produced by the bacteria.

The class of bactericides which we have found to be effective against parodontosis are the formaldehyde carriers, that is non-toxic derivatives containing formaldehyde in combination. British Pat. No. 1124285 discloses one class of such compounds, namely compounds of general formula

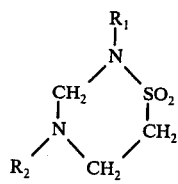 I in which $R_1$ is hydrogen or a straight or branched alkyl group having 1-6 carbon atoms, for example a methyl, ethyl, propyl, isopropyl, butyl, isobutyl, amyl or hexyl group and $R_2$ is hydrogen or a group of the formula

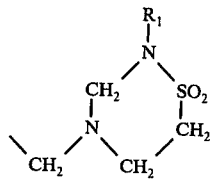

(wherein $R_1$ is as defined above).

The preparation of representative ones of the compounds of formula I are described in Examples 1-18 of the aforementioned British Pat. No. 1,124,285 as follows:

Thus according to one feature of the present invention there is provided a tooth preparation for the treatment and/or prophylaxis of parodontosis comprising, as active ingredient, at least one compound of formula I (as hereinbefore defined).

We have found, however, that the compound of choice is bis-(1,1-dioxo-perhydro-1,2,4-thiadiazinyl-4)-methane (Taurolin) in view of its extremely low toxicity when given over long periods. On the other hand, compounds in which $R_1$ is alkyl tend to have enhanced affinity for the gum which improves their effectiveness.

As indicated, the production of this compound and of the other compounds of formula I is described in British Pat. No. 1124285.

It is noteworthy that the formaldehyde carriers here concerned are effective in treatment of paradontosis, while chlorhexidine, which has been previously suggested for treatment of parodontosis, is not active against the bacterial toxins and is consequently incapable of complete treatment of the disease. Furthermore, the chlorhexidine digluconate solutions which have previously been used have the disadvantage of causing yellowness of the teeth and further have an unpleasant bitter taste. In addition, chlorhexidine is known to produce p-chloroaniline, a very toxic substance, on degredation, so that it is not suitable for long-term treatment of mouth conditions.

In general, the concentration of the active substance in tooth preparations will be higher in the therapeutic treatment of an established parodontosis than in the prophylactic treatment of the teeth to prevent such disease. For therapeutic purposes, the tooth preparations should contain 1-3%, preferably about 2%, of the active material, while for prophylaxis, the preparations should contain 0.5-1.5% of active material, preferably about 1%.

The tooth preparations into which the active material will be incorporated will primarily be toothpastes, both of the foaming and non-foaming types, tooth gels and mouth washes.

A toothpaste according to the invention may be of conventional composition and may, therefore, contain such ingredients as thickening or binding agents, humectants foaming agents, cleansing agents, preservatives, sweeting agents, flavouring agents and water.

Thickening or binding agents will in general be hydrophilic colloids of relatively high viscosity so as to give a creamy consistency to the paste and may, for example, be substances such as carboxymethylcellulose, methylcellulose, alignates, caragheenins hydroxyethylcellulose, polyvinylpyrrolidone or silicic acid. In general, the quantity of binding or thickening agents will be widely variable, according to the nature of the other components and may vary from 1% up to 30% or more.

Humectants may include such compounds as glycerol, sorbitol or propylene glycol; these substances may constitute a relatively large proportion of the composition, for example 10-30%.

Preservatives which may be present includes such substances as hydroxybenzoic acid esters. Sweetening agents include such substances as saccharine or sodium cyclamate. Flavouring agents include various aromatic oils, for example the traditional mint flavour oils.

The cleansing agent will, in general, be a very fine crystalline powder capable of producing light abrasion. The most suitable substance is calcium phosphate dihydrate, but other substances may be used including calcium carbonate, calcium pyrophosphate, aluminium hydroxide aluminium oxide, calcium lactate, magnesium oxide, magnesium carbonate and precipitated silica.

In general, a relatively small quantity of surface active material will be present to assist cleansing of the teeth, even when the toothpaste is not intended to foam. A wide variety of surfactants are available. One particularly suitable class are polyoxyethylene derivatives of sugar alcohol mono-esters, such as polyoxyethlene sorbitan monolaurate and monostearate. Another product of this type is the polyoxyethylene derivative of castor oil sold under the trade name Cremophor EL. It will be appreciated, however, that the very wide range of similar materials may be selected from the conventional surfactants available. In general, a non-ionic surfactant is preferred. In non-forming preparations, the quantity of such non-ionic surfactants will be of the order of 0.5–1.5%

Where a foaming toothpaste is required, it is preferred to incorporated an anionic surfactant, such as a long-chain sulphate or sulphonate salt, for example sodium lauryl sulphate. These substances may, for example, be present at a level of 1–3%, e.g. about 2%.

The water present is preferably deionised, to avoid problems in formulation.

It will be appreciated that many variants in the toothpaste formulations according to the invention are possible and the foregoing is not intended as an exhaustive list of the components which are possible.

Tooth gels will, in general, be very closely similar to toothpaste but will lack the abrasive tooth cleaning material and will thus generally be relatively optically clear. A medically exceptable dye will commonly be present in such formulations.

Mouth washes according to the invention may, again, be of the conventional type and will include, for example, sweetening and flavouring agents, surfactants and, commonly, ethanol. Surfactants which may be present include nonionic surfactants such as the polyoxethylene derivatives mentioned above in relation to toothpastes, as well as the anionic surfactants also mentioned above. In general, mouth washes will be used therapeutically and will therefore contain the active material at the higher level as mentioned above.

Preparations according to the invention may, if desired, contain at least one further active ingredient such as, for example, a substance active agents the production of bacterial plaque, for example sodium benzoate, high molecular polyphosphates, sodium metaphosphate, magnesium tartrate, polyvinylpyrrolidone, polysiloxanes or sodium sulphoricinoleate. Similarly, preparations may contain substances active against caries, for example fluorine compounds.

The following Examples are given by way of illustration only.

EXAMPLE 1: Tooth gel 21,0% Sident 3 (Silicic acid: Degussa)
29,0% Glycerine
28,0% Karion F liquid (70% Sorbitol solution: E. Merck, Darmstadt)
13,0% Propylene glycol
3,75% Water (deionised)
0,05% Saccharine (pure)
1,0% Taurolin
0,4% Tween 20 (Polyoxethylen-Sorbitan-mono-laurate: Atlas)
0,8% Tween 60 (Polyoxethylen-Sorbitan-mono-stearate: Atlas)
1,0% Oleum menthae
2,0% Texapon K 12 (Sodiumlauryl salate: Henkel/Dehydag)

EXAMPLE 2: Tooth gel, foaming 2,0% Texapon K 12
1,0% Taurolin
1,5% Natrosol HR 250 (Hydroxylethyl-Cellulose: Hercules Powder)
10,0% Kollidon 30 or 17 (Polyvinylpyrrolidone: BASF)
0,5% Carmoisine B (Fast RED E) C.I. 16045 (Red dye)
82,8% Water (deionised)
0,5% Saccharine 10% Solution
0,8% Tween 60
0,4% Tween 20
0,5% Oleum menthae EXAMPLE 3: Tooth gel, non-foaming 1,0% Taurolin
1,5% Natrosol HR 250
10,0% Kollidon 30 or 17
0,5% Carmoisine B (Fast RED E) C.I. 16045
3,0% Cremophor EL (Castor-oil-ethyleneoxide adduct: BASF)
0,5% Oleum menthae
1,0% Ethanol
0,5% Saccharine 10% solution
82,0% Water (deionised)

EXAMPLE 4: Tooth gel, non-foaming 1,0% Carbopol 934 (Acrylic acid polymer: B.F. Goodrich)
5,0% Kollidon 30 or 17
1,0% Taurolin
0,3% Carmoisine B (Fast RED E) C.I. 16045
90,5% Water (deionised)
0,5% Saccharine 10% solution
0,5% Oleum menthae
0,8% Tween 60
0,4% Tween 20
ph adjusted to 7 with Triethanolamine EXAMPLE 5: Tooth gel, non-foaming 1,0% Carbopol 940
5,0% Kollidon 30 or 17
1,0% Taurolin
0,5% Carmoisine B (FAST RED E) C.I. 16045
88,5% Water (deionised)
0,5% Saccharine 10% solution
0,5% Oleum menthae
3,0% Cremophor EL EXAMPLE 6: Tooth gel, non-foaming 1.0% Taurolin
1,5% Natrosol HR 250
10,0% Kollidon 30
0,5% Carmoisine B (Fast RED E) C.I. 16045
0,5% Oleum menthae
2,0% Ethanol
4,0% Saccharine 1,0% solution 1,0% Cremophor EL (Castor-oil with Aethylenoixid-Product: BASF)
79,5% Water (deionised)

EXAMPLE 7: Tooth gel, non-foaming 1,0% Carbopol 941
5,0% Kollidon 30 or 17
1,0% Taurolin
0,5% Carmoisine B (Fast RED E) C.I. 16045
90,3% Water (deionised)
0,5% Oleum menthae
0,8% Tween 60
0,4% Tween 20

0,5% Saccharine 10% solution

EXAMPLE 8: Toothpaste, foaming 1,0% Methocell 4000 cps. (Methyl cellulose: Dow Chemical Midland Mich. USA)
1,0% Taurolin
23,05% Water (deionised)
19,0% Propyleneglycol
9,3% Glycerin
(o,25% Nipagin M* (Methyl p-hydroxybenzoate: Nipa Laboratories Treforest, Pontypridd)
0,5% Saccharine 10% solution
1,2% Paraffin oil
1,0 Oleum menthae
2,0% Texapon K 12
41,7% Calcium phosphate dihiydrate
* can be omitted

EXAMPLE 9% Toothpaste, foaming 1,0% Methocell 4000 cps.
1,0% Taurolin
21,7% Water (deionised)
19,0% Propylene glycol
9,3% Glycerine
0,5% Saccharine 10% solution
1,0% Paraffin oil
1,0% oleum methae
2,0% Texapon K 12
43,5% Calcium carbonate (precipitated)

EXAMPLE 10: Toothpaste, foaming 33,0% Calcium carbonate (precipitated)
34,8% Water (deionised)
20,0% Glycerine
3,0% Sorbitol (Fine silicic acid: Degussa)
2,0% Aerosil
2,0% Texapon K 12
1,0% Oleum menthae
1,2% Texamid 578 L (Sodium Alignate: Henkel/Dehydag)
1,0% Paraffin oil perl
1.0% Taurolin
1,0% Saccharine 10% solution

EXAMPLE 11: Mouth wash 79,0% Water (deionised)
2,0% Taurolin
1,0% Texapon K 12
15,0% Ethanol
0,5% Saccharine 10% solution
0,5% Oleum menthae
2,0% Tween 80 (Polyoxyethylene-sorbinanmonooleate: Atlas)

EXAMPLE 12: Mouth wash 73,8% Desalinated water
2,0% Taurolin
10,0% Ethanol
1,5% Parfum dentifrice 24/45 (Charabot, France)
0,2% Methol cristalline (Charabot, France)
5,0% Tinct. arnica
5,0% Hamaelis Extract
0,5% Kamillen Extract
2,0% Texapon K 12

We claim:

1. A method of treatment or prophylaxis of parodontosis comprising applying to the teeth and gums of the subject an effective amount of at least one compound of formula

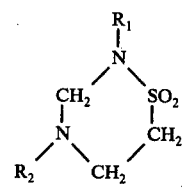

I wherein $R_1$ represents a hydrogen atom or a straight or branched alkyl group having from 1 to 6 carbon atoms, and $R_2$ represents a hydrogen atom or a group of formula

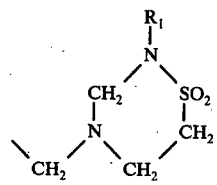

wherein $R_1$ is as defined above.

2. A method as claimed in claim 1 wherein the compound applied is bis-(1,1-dioxo-perhydro-1,2,4-thiadiazinyl-4)methane.

3. A method as claimed in claim 1 wherein the compound is applied in the form of a toothpaste, toothgel or mouthwash.

4. A method as claimed in claim 1 wherein the compound is applied together with at least one substance active against the production of bacterial plaque or caries.

5. A method as claimed in claim 2 for the treatment of parodontosis wherein there is applied a preparation containing from 1 to 3% of said compound.

6. A method as claimed in claim 2 for the prophylaxis of parodontosis wherein there is applied a preparation containing from 0.5 to 1.5% of said compound.

* * * * *